United States Patent [19]

Degner et al.

[11] Patent Number: 4,847,425

[45] Date of Patent: Jul. 11, 1989

[54] PREPARTION OF 4-ISOPROPYLCYCLOHEXYLMETHANOL AND ITS ALKYL ETHERS

[75] Inventors: Dieter Degner, Dannstadt-Schauernheim; Walter Gramlich, Edingen-Neckarhausen; Wolfgang Lengsfeld; Ludwig Schuster, both of Limburgerhof, all of Fed. Rep. of Germany

[73] Assignee: BASF Aktiengesellschaft, Ludwigshafen, Fed. Rep. of Germany

[21] Appl. No.: 200,460

[22] Filed: May 31, 1988

[30] Foreign Application Priority Data

Jun. 3, 1987 [DE] Fed. Rep. of Germany ....... 3718564

[51] Int. Cl.$^4$ ..................... C07C 29/14; C07C 41/28; C07C 31/135; C07C 43/115
[52] U.S. Cl. .................................. 568/579; 568/831; 585/357
[58] Field of Search ................. 568/579, 831; 585/357

[56] References Cited

U.S. PATENT DOCUMENTS

| | | | |
|---|---|---|---|
| 2,599,089 | 6/1952 | Castle et al. | 585/357 |
| 3,366,695 | 1/1968 | Lundeen | 568/831 |
| 3,993,604 | 11/1976 | Thomas et al. | 426/538 |
| 4,338,475 | 7/1982 | Pennington et al. | 585/357 |
| 4,413,149 | 11/1983 | Fischer et al. | 568/636 |
| 4,433,188 | 2/1984 | Hoelderich et al. | 585/357 |
| 4,479,017 | 10/1984 | Ayusawa et al. | 568/613 |
| 4,695,660 | 9/1987 | Otte et al. | 568/830 |

FOREIGN PATENT DOCUMENTS

| | | |
|---|---|---|
| 0054699 | 6/1982 | European Pat. Off. . |
| 0059373 | 9/1982 | European Pat. Off. . |
| 0222984 | 5/1987 | European Pat. Off. . |
| 1952725 | 4/1971 | Fed. Rep. of Germany ...... 585/357 |
| 3224033 | 1/1983 | Fed. Rep. of Germany . |
| 3644076 | 12/1986 | Fed. Rep. of Germany . |

OTHER PUBLICATIONS

Reduction in Organic Chemistry, M. Hudlicky, 1984, p. 99.
Hydrogenation Methods, P. N. Rylander, 1985, p. 157.

*Primary Examiner*—J. E. Evans
*Assistant Examiner*—Karen E. Kulesza
*Attorney, Agent, or Firm*—Oblon, Spivak, McClelland, Maier & Neustadt

[57] ABSTRACT

4-isopropylcyclohexylmethanol and its alkyl ethers of the general formula I

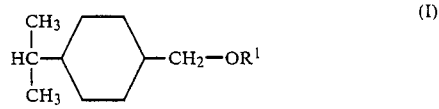

where $R^1$ is H or $C_1$–$C_4$-alkyl, are prepared by a process in which the novel 4-(1-alkoxy-1-methylethyl)-benzaldehyde or its dialkyl acetal of the general formula II

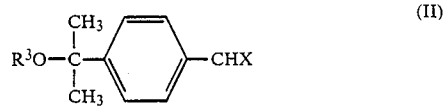

where X is oxygen (IIa) or its two $R^2O$ groups (IIb) and $R^2$ and $R^3$ are each $C_1$–$C_4$-alkyl, is heated to 100°–250° C., preferably 130°–200° C., under a hydrogen pressure of from 50 to 350, preferably from 150 to 300, bar in the presence of a noble metal of group VIII of the Periodic Table.

7 Claims, No Drawings

PREPARTION OF 4-ISOPROPYLCYCLOHEXYLMETHANOL AND ITS ALKYL ETHERS

German Laid-Open Application DOS 2,427,609 (or U.S. Pat. No. 3,993,604) describes novel acyclic compounds of the general formula III

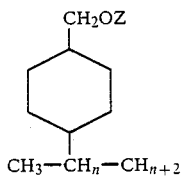

which have a single bond or a double bond in the position indicated by the dashed line and in which n is 0 or 1 and Z is hydrogen or an alkyl or acyl group of 1 to 6 carbon atoms.

The most important compound in this class is 4-isopropylcyclohexylmethanol (where Z is H, n is 1 and the dashed line is a single bond), sold under the trade name Mayol ® and its ethyl ether (where Z is $C_2H_5$, n is 1 and the dashed line is a single bond).

The patent specifications mentioned describe a process for the preparation of 4-isopropylcyclohexylmethanol which is based on hydrogenation of the nucleus of cuminaldehyde of the formula IV

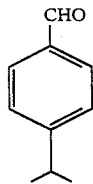

The disadvantage of this process is that the cuminaldehyde is expensive to obtain.

Furthermore, the preparation of the ethers of the formula III (where Z is alkyl) according to the stated publications is very unsatisfactory. In this preparation, the appropriate alcohols are reacted with sodium hydride in dimethyl sulfoxide (DMSO) and the product is then alkylated with an alkyl halide. Although this method is certainly easy to perform on the laboratory scale, it is today demanding and expensive to carry out on a large industrial scale because of the difficulty of handling the sodium hydride/DMSO mixture, because of the molar amounts of salt (NaBr) formed by the reaction with alkyl halides and because of the DMSO which enters the wastewater during washing. Furthermore, for toxicological reasons, the use of alkyl halides is not entirely without problems, since some of these are potential carcinogens.

It is an object of the present invention to provide a process for the preparation of 4-isopropylcyclohexylmethanol and its alkyl ethers, in which more readily obtainable and therefore cheaper starting compounds can be employed and which can be carried out very simply and without a high toxicological risk.

We have found that this object is achieved and that, surprisingly, the novel 4-(1-alkoxy-1-methylethyl)benzaldehyde, lately very readily obtainable from p-cymene by an electrochemical method according to the non-priorpublished German Laid-Open Application DOS ...... (P 36 44 076.0), can be converted to the desired 4-isopropylcyclohexylmethanol in virtually quantitative yield by catalytic hydrogenation at above 100° C. with elimination of alkanols (from the alkoxy group and hydrogen), hydrogenation of the resulting double bond, and hydrogenation of the aromatic nucleus and of the aldehyde group. If, instead of the stated benzaldehyde, its dialkyl acetal is used as the starting compound, the corresponding alkyl ether is obtained, likewise in virtually quantitative yield, with elimination of two moles of alkanol (ie. alkoxy groups and hydrogen), hydrogenation of the resulting double bonds and hydrogenation of the nucleus.

The present invention therefore provides a process for the preparation of 4-isopropylcyclohexylmethanol or its alkyl ethers of the general formula I

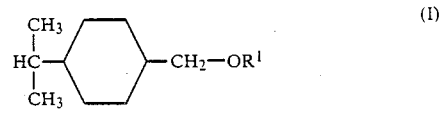

where $R^1$ is H or $C_1C_4$-alkyl, wherein the novel 4-(1-alkoxy-1-methylethyl)-benzaldehyde or its dialkyl acetal of the general formula II

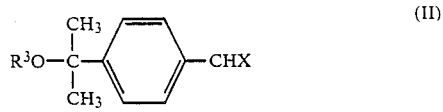

where X is oxygen (IIa) or is two $R^2O$ groups (IIb) and $R^2$ and $R^3$ are each $C_1-C_4$-alkyl, is heated to 100°–250° C., preferably 130°–200° C., under a hydrogen pressure of from 50 to 350, preferably from 150 to 300, bar in the presence of a noble metal of group VIII of the Periodic Table.

The novel 4-(1-alkoxy-1-methylethyl)-benzaldlehyde diacetals IIb used as starting materials are obtained in a relatively simple manner by electrochemical oxidation of the corresponding 4-(1-alkoxy-1-methylethyl)-toluenes in the presence of a lower alcohol. Hydrolysis with water converts these diacetals IIb into the benzaldehydes IIa in very good yields.

Suitable noble metals of group VIII of the Periodic Table are essentially the known hydrogenation catalysts, such as nickel (in the form of Raney nickel), palladium, platinum, rhodium and ruthenium. Ruthenium has proven particularly advantageous. In general, the noble metals are applied to a catalyst carrier, such as alumina or active carbon, in amounts of from 0.5 to 10% by weight, based on the carrier, before being used. However, it is also possible to employ the pure metals or metal compounds.

The reaction conditions, ie. catalysts, solvents, reaction temperature, hydrogen pressure and reaction time, can be varied within relatively wide limits. Temperatures of from 100 to 250° C. are preferably used. Below 100° C., virtually no alkanol is eliminated. Hydrogen pressures are usually from 50 to 350, preferably from 150 to 300, bar.

Examples of suitable solvents for the hydrogenation are alkanols, such as methanol or ethanol, ethers, such as tetrahydrofuran, hydrocarbons, such as pentane, and acids, such as acetic acid; the hydrogenation can, however, also be carried out in the absence of a solvent.

The hydrogenation of 4-(1-alkoxy-1-methylethyl)-benzaldehyde (IIa) gives mixtures of the cis and transisomers; when the preferred ruthenium catalyst is used, the cis/trans ratio is from 60 : 40 to 70 : 30.

The parameters of the reaction can be chosen so that the resulting intermediates

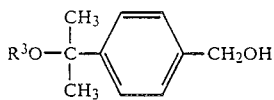

V

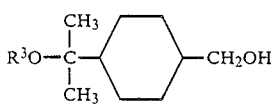

VI 4-(1-alkoxy-1-methylethyl)-benzyl alcohol (V) and 4-(1-alkoxy-1-methylethyl)-cyclohexylmethanol (VI) can be isolated, although these intermediates are unimportant in terms of olfactory properties.

The ethers of the formula I which are obtained from the acetals IIb in the hydrogenation also occur in the form of cis/transisomers. In this case too, the cis/transisomer ratio is from 60 : 40 to 70 : 30.

With the aid of the novel process, the compounds of the formula I, which are very desirable scents, can be prepared in a very elegant manner from novel but readily available starting compounds. In particular, the considerable disadvantages described for the preparation of the ethers of the formula I according to the prior art cited have been avoided. Moreover, in the novel process the dialkyl acetals IIb are the intermediates for the preparation of the corresponding aldehydes and hence two process steps are additionally dispensed with.

The Examples which follow illustrate the process.

EXAMPLE 1

A. Electrosynthesis of 4-(1-methoxy-1-methylethyl)-benzaldehyde dimethyl acetal from 4-(1-methoxy-1-methylethyl)-toluene Apparatus: undivided cell containing 5 electrodes, electrode spacing: 1.5 mm.

Anodes: graphite; cathodes: graphite.

In a first batch, an electrolyte having the following composition was used for the electrolysis: 14.03 kg of 4-(1-methoxy-1-methylethyl)-toluene, 0.63 kg of $KSO_3C_6H_5$, 0.16 kg of $C_6H_5SO_3H$ and 62.2 of $CH_3OH$.

The electrolysis was carried out using 11 F/mole of 4-(1-methoxy-1-methylethyl)-toluene at a current density of 3.6 A/dm$^2$ and at 26° C. The electrolyte was pumped through the cell at a rate of 800 L/h, via a heating exchanger.

In a second batch, the electrolysis was carried out similarly, using the following electrolyte: 11.83 kg of 4-(1-methoxy-1-methylethyl)-toluene, 0.68 ig of $KSO_3C_6H_5$, 0.17 kg of $C_6H_5SO_3H$ and 67.7 kg of $CH_3OH$.

When the electrolyses were complete, the two electrolysis solutions discharged were combined and were worked up together. Working up procedure:

First, methanol was distilled off under atmospheric pressure up to a bottom temperature of 125° C. The residue was cooled to about 30° C. and filtered over a suction filter. This gave 0.9 kg of a salt, which could be recycled to the electrolysis together with the methanol. The filtrate (43.3 kg) was then rectified under a top pressure of 2 mbar and at 100°-120° C. (top temperatures). This procedure gave 0.17 kg of 4-(1-methoxy-1-methethyl)toluene, 1.54 kg of 1-methoxymethyl-4-(1-methoxy-1-methylethyl)-benzene and 20.88 kg of 4-(1-methoxy-1-methylethyl)benzaldehyde dimethyl acetal. This correponds to a conversion of 99.3%, based on 4-(1-methoxy-1-methylethyl)toluene, a yield of 5% of 1-methoxymethyl-4-(1-methoxy-1-methylethyl)-benzene and a yield of 59.1% of 4-(1-methoxy-1-methylethyl)benzaldehyde dimethyl acetal. The selectivity for the dimethyl acetal was 62.7%. The unconverted starting compound and the 1-methoxymethyl-4-(1-methoxy-1-methylethyl)-benzene could be recycled to the electrolysis.

B. Preparation of 4-isopropylcyclohexylmethyl methyl ether

In an autoclave, a solution of 575 g (2.57 moles) of the starting material obtained according to A, 4-(1-methoxy-1-methylethyl)-benzaldehyde dimethyl acetal, in 600 ml of tetrahydrofuran (THF) was flushed several times with nitrogen and hydrogen in the presence of 9 g of ruthenium hydroxide and then hydrogenated at 130° C. and under hydrogen pressure of 200 bar until the pressure remained constant.

After the catalyst had been removed, the THF was first distilled off and the residue was then subjected to fractional distillation under 10 mbar.

410 g (94% yield) of 4-isopropylcylohexylmethyl methyl ether, a substance not yet described as such, were obtained in the form of a 65 : 35 cis/trans mixture. Bp. 42° C./0.3 mbar, $n_D^{25} = 1.4465$

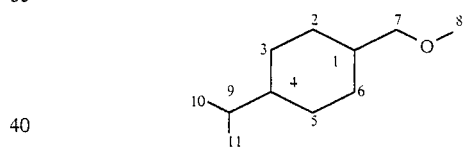

IR: 2955, 2922, 2869, 2855, 1449, 1385, 1197, 1117 cm$^{-1}$.

$^{13}$C-NMR (cis-isomer): δ=75.67 (C$_7$,t), 58.72 (C$_8$,q), 43.05 (C$_4$,d), 34.70 (C$_1$,d), 30.52 (C$_9$,d),26.59 (C$_6$ and C$_2$,t), 25.80 (C$_3$ and C$_5$,t), 20.28 (C$_{10}$ and C$_{11}$, q) ppm.

$^{13}$C-NMR (trans isomer): δ=79.00 (C$_7$,t), 58.72 (C$_8$,q), 44.36 (C$_4$,d), 38.34 (C$_1$,d), 33.0 (C$_9$,d), 30.27 (C$_6$ and C$_2$,t), 29.33 (C$_3$ and C$_5$,t), 19.86 (C$_{10}$ and C$_{11}$, q) ppm.

MS (m/e): M$^+$: 170 (0.1%), 138 (38), 123 (12), 109 (26), 95 (100), 81 (28), 69 (54), 55 (32), 45 (50), 41 (35).

EXAMPLE 2

A. Preparation of 4-(1-methoxy-1-methylethyl)-benzaldlehyde from 4-(1-methoxy-1-methylethyl)-benzaldehyde dimethyl acetal 1.9 kg of 4-(1-methoxy-1-methylethyl)-benzaldehyde dimethyl acetal and 1.8 kg of water were refluxed (bottom temperature 87° C.) for about 1 hour, while stirring. Thereafter, the mixture was cooled to about 25° C., the phases were separated and the organic phase was distilled under a top pressure of 4 mbar and at 105°-108° C. (top temperatures). This gave 1,314.6 kg of 4-(1-methoxy-1-methylethyl)-benzaldehyde.

$^1$H-NMR: $(CH_3)_2C-$: 1.55 ppm (s), $-OCH_3$: 3.1 ppm (s), ArH: 7.6 ppm (d), 7.90 ppm (d), $-CHO$: 10.0 ppm(s), $n_D^{25} = 1.5264$ This corresponds to a yield of 97.3%.

B. Preparation of 4-isopropylcyclohexylmethyl methyl ether

In an autoclave, 405 g (2.5 moles) of the 4-(1-methoxy-1-methylethyl)-benzaldehyde obtained according to A, in 200 ml of THF, were flushed several times with nitrogen and hydrogen in the presence of 1 g of ruthenium hydroxide and then hydrogenated at 150° C. and under a hydrogen pressure of 300 bar until the pressure remained constant.

After the catalyst had been removed, the THF was first distilled off and the residue was then subjected to fractional distillation under 10 mbar. A diastereomer mixture having a cis/trans ratio of 65 : 35 was obtained.

The two cis and trans isomers were separable in pure form as described in German Laid-Open Application DOS 2,427,609, by an expensive distillation (spinning band column, Laboratory Sulzer column), and had properties identical to the data given in the Literature [J. Org. Chem. 31 (1966), 3507].

We claim:

1. A process for the preparation of 4-isopropylcyclohexylmethanol or its alkyl ethers of the formula I

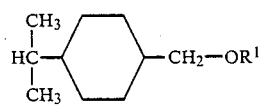

(I)

where $R^1$ is H or $C_1-C_4$- alkyl, wherein a 4-(1-alkoxy-1-methylethyl)-benzaldehyde or its dialkyl acetal of the formula II

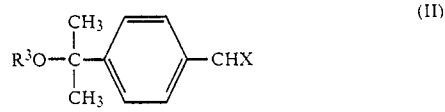

(II)

where X is oxygen (IIa) or is two $R^2O$ groups (IIb) and $R^2$ and $R^3$ are each $C_1-C_4$-alkyl, is heated to 100°–250° C. under a hydrogen pressure of from 50 to 350 bar in the presence of a noble metal or group VIII of the Periodic Table.

2. A process as claimed in claim 1, wherein a compound of the formula II is heated to 130°–200° C.

3. A process as claimed in claim 1, wherein a compound of the formula II is heated under a hydrogen pressure of 150 to 300 bar.

4. A process as claimed in claim 1, wherein a 4-(1-alkoxy-1-methylethyl)-benzaldlehyde is heated in the presence of a noble metal and hydrogen for the preparation of 4-isopropylcyclohexylmethanol.

5. A process as claimed in claim 1, wherein a 4-(1-alkoxy-1-methylethyl)-benzaldehyde dialkyl acetal is heated in the presence of a noble metal and hydrogen for the preparation of a 4-isopropylcyclohexylmethyl alkyl ether.

6. A process as claimed in claim 1, wherein nickel, rhodium, palladium, platinum or ruthenium is used as the noble metal of group VIII of the Periodic Table.

7. A process as claimed in claim 1, wherein ruthenium is used as the noble metal of group VIII of the Periodic Table.

* * * * *